(12) United States Patent
Halldorsson

(10) Patent No.: US 9,498,355 B2
(45) Date of Patent: *Nov. 22, 2016

(54) SUSPENSION LINER HAVING MULTIPLE COMPONENT SYSTEM

(71) Applicant: OSSUR HF, Reykjavik (IS)

(72) Inventor: Olafur Freyr Halldorsson, Reykjavik (IS)

(73) Assignee: OSSUR HF, Reykjavik (IS)

( * ) Notice: Subject to any disclaimer, the term of this patent is extended or adjusted under 35 U.S.C. 154(b) by 80 days.

This patent is subject to a terminal disclaimer.

(21) Appl. No.: 14/474,618

(22) Filed: Sep. 2, 2014

(65) Prior Publication Data

US 2014/0371873 A1 Dec. 18, 2014

Related U.S. Application Data

(63) Continuation of application No. 12/947,944, filed on Nov. 17, 2010, now Pat. No. 8,828,094.

(60) Provisional application No. 61/261,863, filed on Nov. 17, 2009.

(51) Int. Cl.
| | | |
|---|---|---|
| *A61F 2/78* | (2006.01) | |
| *A61F 2/80* | (2006.01) | |
| *A61F 2/50* | (2006.01) | |

(52) U.S. Cl.
CPC ............... *A61F 2/80* (2013.01); *A61F 2/7812* (2013.01); *A61F 2002/5056* (2013.01); *A61F 2002/785* (2013.01); *A61F 2002/7818* (2013.01); *A61F 2240/001* (2013.01); *A61F 2250/0014* (2013.01); *A61F 2250/0018* (2013.01)

(58) Field of Classification Search
CPC .................................. A61F 2/7812–2002/785
See application file for complete search history.

(56) References Cited

U.S. PATENT DOCUMENTS

| | | |
|---|---|---|
| 3,587,572 A | 6/1971 | Evans |
| 4,908,037 A | 3/1990 | Ross |
| 4,923,474 A | 5/1990 | Klasson et al. |
| 5,263,923 A | 11/1993 | Fujimoto |
| 5,308,305 A | 5/1994 | Romney |
| 5,376,129 A | 12/1994 | Faulkner et al. |
| 5,507,834 A | 4/1996 | Laghi |

(Continued)

FOREIGN PATENT DOCUMENTS

| | | |
|---|---|---|
| CN | 1427701 A | 7/2003 |
| CN | 201088641 Y | 7/2008 |

(Continued)

OTHER PUBLICATIONS

International Search Report and the Written Opinion of the International Searching Authority from International Application No. PCT/US2014/055070, Nov. 21, 2014.

(Continued)

*Primary Examiner* — David H Willse
(74) *Attorney, Agent, or Firm* — Workman Nydegger

(57) ABSTRACT

A residual limb suspension liner for a prosthesis has a first layer defined by a first elastomeric material and forms a continuous circumferential internal surface of the liner. The liner also includes a second layer defined by a second elastomeric material different from the first elastomeric material. The second layer has a first surface adjacent to and integrally joined to the first layer. The second layer has a variable radial thickness over an anterior aspect of the liner.

12 Claims, 3 Drawing Sheets

(56) References Cited

U.S. PATENT DOCUMENTS

| | | |
|---|---|---|
| 5,718,925 A | 2/1998 | Kristinsson et al. |
| 5,728,167 A | 3/1998 | Lohmann |
| 5,830,237 A | 11/1998 | Kania |
| 5,888,216 A | 3/1999 | Haberman |
| 5,971,729 A | 10/1999 | Kristinsson et al. |
| 5,972,036 A | 10/1999 | Kristinsson et al. |
| 6,110,134 A | 8/2000 | Clark, Jr. et al. |
| 6,136,039 A | 10/2000 | Kristinsson et al. |
| 6,231,617 B1 | 5/2001 | Fay |
| 6,416,703 B1 | 7/2002 | Kristinsson et al. |
| 6,485,776 B2 | 11/2002 | Janusson et al. |
| 6,592,539 B1 | 7/2003 | Einarsson et al. |
| 6,706,364 B2 | 3/2004 | Janusson et al. |
| 6,918,936 B2 | 7/2005 | Hellberg |
| 6,964,688 B1 | 11/2005 | Kania |
| 7,001,563 B2 | 2/2006 | Janusson et al. |
| 7,025,793 B2 | 4/2006 | Egilsson |
| 7,118,602 B2 | 10/2006 | Bjarnason |
| 7,169,189 B2 | 1/2007 | Bjarnason et al. |
| 7,749,281 B2 | 7/2010 | Egilsson |
| 7,909,884 B2 | 3/2011 | Egilsson et al. |
| 8,034,120 B2 | 10/2011 | Egilsson et al. |
| 8,052,760 B2 | 11/2011 | Egilsson et al. |
| 8,382,852 B2 | 2/2013 | Laghi |
| 8,828,094 B2 | 9/2014 | Halldorsson |
| 2005/0101693 A1 | 5/2005 | Arbogast et al. |
| 2005/0149202 A1 | 7/2005 | Schaffer et al. |
| 2006/0106328 A1 | 5/2006 | Sieller et al. |
| 2006/0111792 A1 | 5/2006 | Shannon |
| 2007/0061017 A1 | 3/2007 | Wilson |
| 2007/0123998 A1 | 5/2007 | Egilsson et al. |
| 2007/0162153 A1 | 7/2007 | Barnes et al. |
| 2009/0036999 A1 | 2/2009 | Egilsson et al. |
| 2009/0132056 A1 | 5/2009 | Kania |
| 2010/0016993 A1 | 1/2010 | Mackenzie |
| 2011/0118854 A1 | 5/2011 | Halldorsson |
| 2011/0270414 A1 | 11/2011 | Laghi et al. |
| 2013/0085435 A1 | 4/2013 | Murphy et al. |

FOREIGN PATENT DOCUMENTS

| | | |
|---|---|---|
| DE | 2 127 269 A1 | 12/1972 |
| DE | 100 40 955 A1 | 3/2002 |
| SU | 1739990 A1 | 6/1992 |
| WO | 97/17917 A1 | 5/1997 |
| WO | 2011/062619 A1 | 5/2011 |

OTHER PUBLICATIONS

International Search Report from PCT Application No. PCT/US2010/002990, Feb. 21, 2011.

Written Opinion of the International Searching Authority Corresponding to PCT Application No. PCT/US2010/002990, Feb. 21, 2011.

Office Action from corresponding Chinese Application No. 201080051763.9, Apr. 11, 2014.

International Search Report and Written Opinion of the International Searching Authority from Corresponding International Application No. PCT/US2014/037991, mailed Sep. 23, 2014.

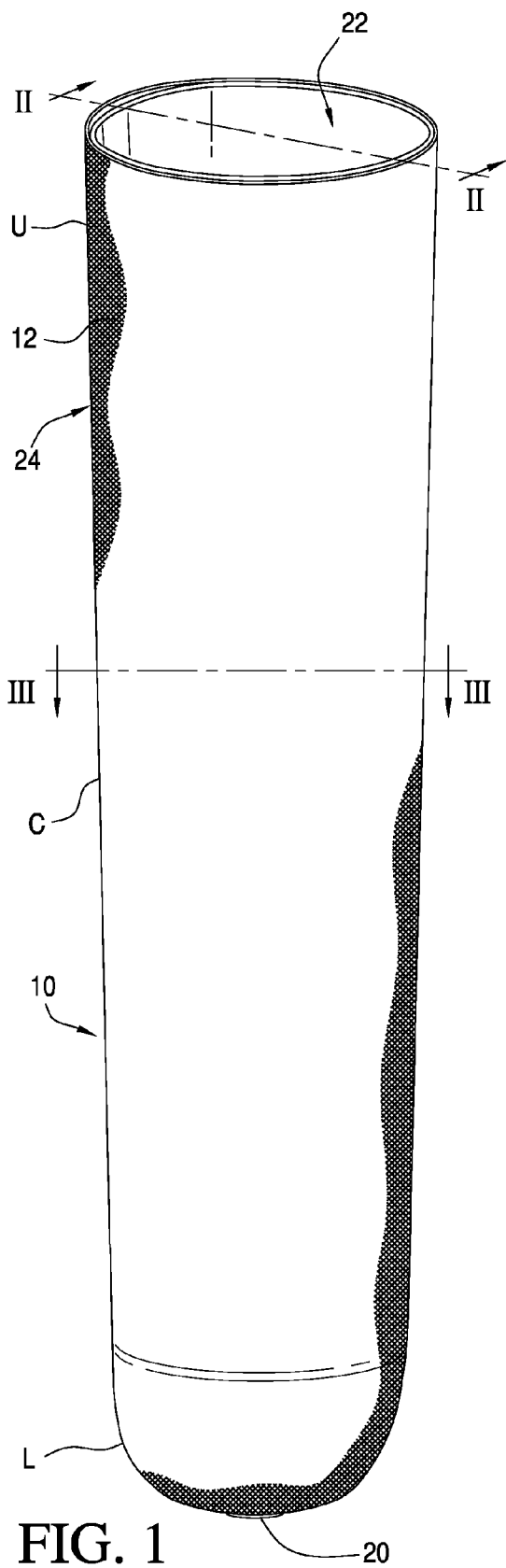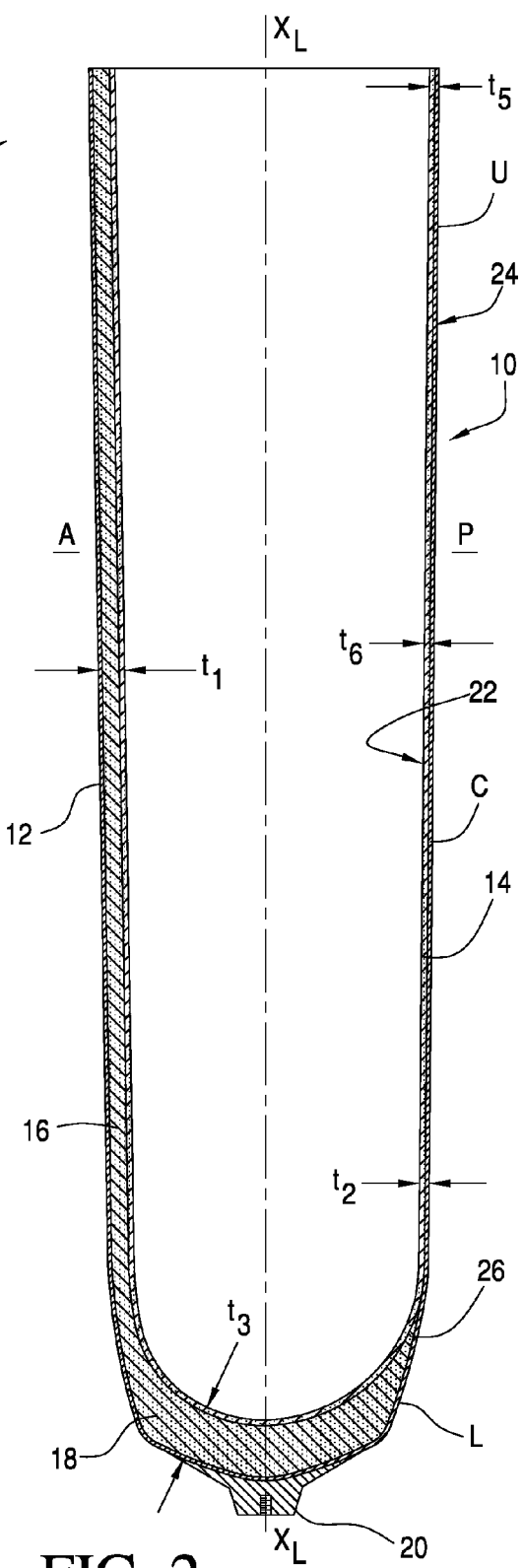

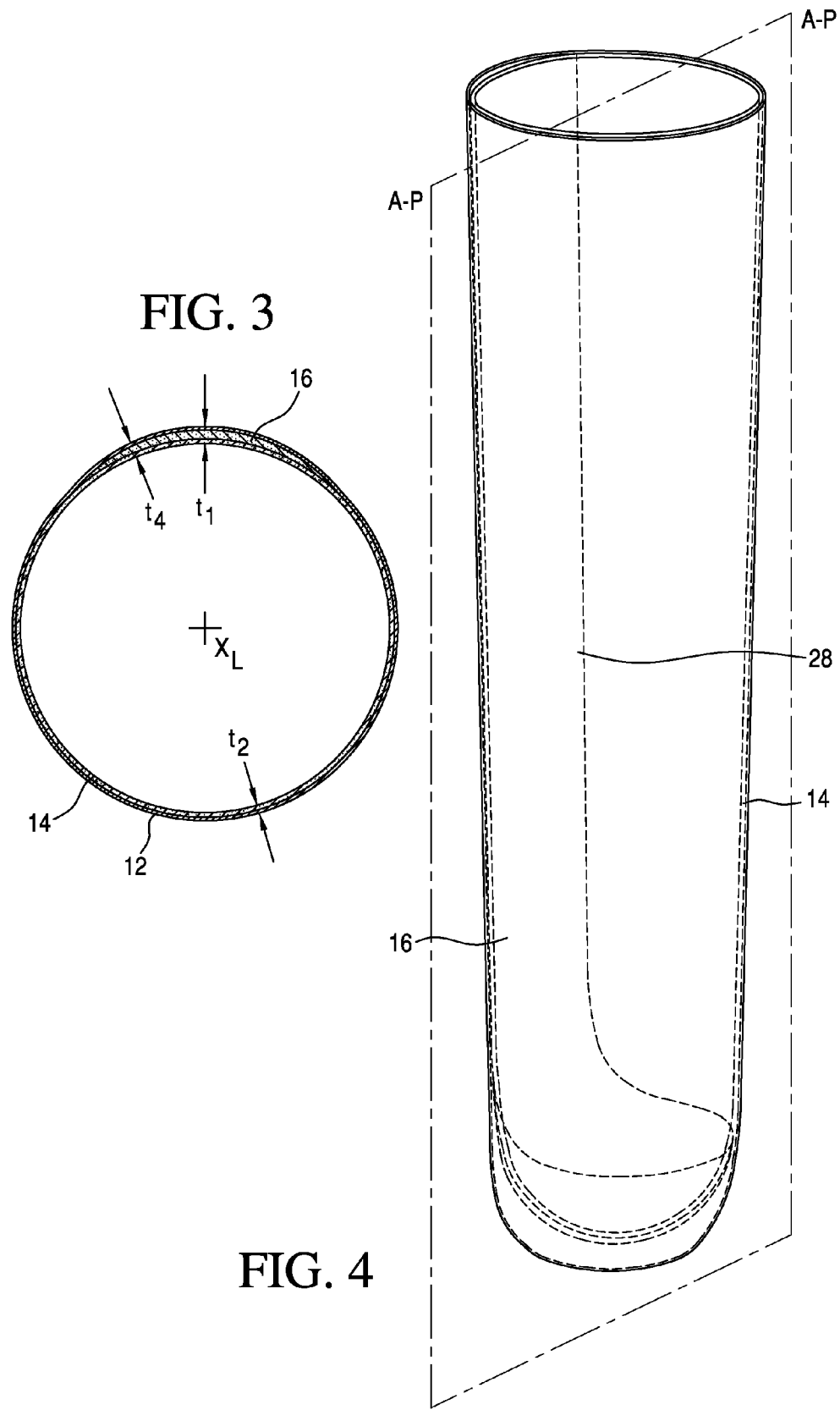

SUSPENSION LINER HAVING MULTIPLE COMPONENT SYSTEM

CROSS-REFERENCE TO RELATED APPLICATIONS

This application is a continuation of U.S. application Ser. No. 12/947,944, filed on Nov. 17, 2010, now U.S. Pat. No. 8,828,094, which claims the benefit of priority of U.S. provisional application No. 61/261,863, filed on Nov. 17, 2009, the entirety of which is incorporated herein by reference.

TECHNICAL FIELD

The present application is directed to a liner or sleeve having a multiple component system, and more specifically to suspension liners formed from a plurality of different layers having different material properties and thicknesses.

BACKGROUND

Prosthetic suspension liners or sleeves have been described in prior patents, such as U.S. Pat. No. 4,923,474, issued May 8, 1990; U.S. Pat. No. 6,136,039, issued Oct. 24, 2000; U.S. Pat. No. 6,485,776, issued Nov. 26, 2002; U.S. Pat. No. 7,118,602, issued Oct. 10, 2006; and U.S. Pat. No. 7,169,189, issued on Jan. 30, 2007, each of which are incorporated herein by reference. These liners or sleeves may be fabricated of elastic or elasticized materials, and are used to cushion a post-operative stump or residual limb with respect to a prosthesis, such as a socket, that is installed over the residual limb and coupled to the liner or sleeve by a conventional locking element.

It is highly desirable that these liners conform closely to the residual limb, accommodate all surface contours and sub-surface bone elements of the residual limb, and provide a comfortable cushion between the residual limb and the hard socket of the prosthesis that is to be fitted over the residual limb.

Special silicone rubber or elastomeric materials have been formulated as suitable substances for suspension liners. Such elastomeric materials having an appropriate hardness (or softness), elongation, tensile, and other properties, such as bio-inertness (resulting in no skin reaction), have been successfully used for suspension liners.

Much like liners, orthopedic or prosthetic sleeves are provided for supporting and reinforcing muscles, joints, and extremities of those in need of assistance, and moreover provide an airtight seal between a residual limb of an amputee and a prosthesis socket worn by the amputee. Moreover, such sleeves are not limited to use for amputees but may be applied to existing limbs to provide support in a manner associated with conventional orthopedic devices. Orthopedic and prosthetic sleeves of this type are described in U.S. Pat. No. 6,592,539 issued Jul. 15, 2003.

These sleeves may be similarly fabricated of elastic or elasticized materials as in liners. Typically, these sleeves are formed by joining sections of elasticized fabric shaped in tubular form and joined at their axial ends to form a tubular sleeve extending in an axial direction. The sleeves may be cylindrical, curved or possess other anatomically conforming shapes.

While effective solutions have been proposed and implemented, it is still highly desirable to improve comfort of such liners or sleeves to increase their ability to conform to irregularities on a residual limb, to accommodate a wider variety of limbs with fewer sizes of liners, and provide an amputee with enhanced comfort at a residual limb interface with a prosthesis while maintaining sufficient strength and durability. Moreover, it is particularly desirable to provide a liner or sleeve wherein means is made available to distribute pressure of the liner against a prosthesis while providing superior stretching over known liners and sleeves.

For the foregoing reasons, there is a need to provide improved liners and sleeves that impart improved conformance, pressure distribution, comfort and stretching while maintaining sufficient durability and strength for their requisite applications.

SUMMARY

In accordance with the illustrated embodiments of the invention, a residual limb suspension liner satisfies the aforementioned needs. The illustrated embodiment displays the liner as being particularly tailored for a prosthesis. The liner forms a closed-ended, tubular sleeve having a longitudinal axis, and defines along the axis a lower portion, an upper portion, and a center portion extending between the lower and upper portions. The liner is also divided along an anterior-posterior plane between anterior and posterior aspects or sides of the liner.

The liner includes a first layer defined by a first elastomeric material and has first and second surfaces spaced by a first thickness. The first surface forms a continuous circumferential internal surface of the liner.

The liner also has a second layer defined by a second elastomeric material and defines first and second surfaces spaced by a second thickness. The second layer first surface is adjacent and integrally joined to the first layer second surface. The second layer has a variable radial thickness over the anterior aspect of the liner. Both the second layer and portions of the first layer may be covered continuously by a fabric layer.

The first layer is preferably stiffer than the second layer, whereas the first elastomeric material has a greater stiffness than the second elastomeric material. The second layer provides cushioning for at least the anterior of the liner, particularly for the tibia of a trans-tibial amputee. The second layer serves as a soft pad over bony areas of a residual limb, to improve skin condition or mitigate issues due to a breakdown of the skin at such areas.

The first layer may continuously extend about anterior and posterior aspects of the internal surface of the liner. The second layer is preferably located only along a posterior aspect of the liner in the lower portion of the liner. The second layer may extend about the entirety of the lower portion of the liner, as well as from the upper and center portions of the liner along the anterior aspect of the liner, and terminate at the lower portion at the posterior aspect.

The thickness of the first layer may be consistently the same about the circumference of the liner. The thickness of the second layer may also vary as extending to first or lateral and second or medial sides of the liner. The thickness of the first layer adjacent the second layer may remain consistently the same. According to a variation of the liner, the second layer may extend less than 50% over the total surface area of the first surface of the first layer.

According to an embodiment of the liner, the second layer second surface forms a plurality of peripheral profiles extending radially outwardly relative to the longitudinal axis. The first layer second surface and the second layer first surface are continuously devoid of the peripheral profiles. The second layer may form an undulating wall thickness along an elongated portion thereof, and the undulating wall thickness may be formed only along the second layer second surface.

The peripheral profile allows for easier knee flexion at the knee with improved cushioning, while the stiffer first layer allows for stability and increased proprioception of the liner, particularly in areas outside of the second layer. The second layer also provides cushioning at the lower or distal end of the liner by increasing the use of softer elastomeric material and a greater thickness of such material.

The increased stability is due in part to a thinner use of the first, stiffer elastomeric material at the posterior aspect of the liner, thereby allowing the residual limb to be in closer contact with a socket worn with the liner to form part of the prosthesis. The increase in stability also attributes to improved control for the amputee.

BRIEF DESCRIPTION OF THE DRAWINGS

The numerous other advantages, features and functions of embodiments of a suspension liner will become readily apparent and better understood in view of the following description and accompanying drawings. The following description is not intended to limit the scope of the suspension liner, but instead merely provides exemplary embodiments for ease of understanding.

FIG. 1 is an elevational view of an embodiment of a suspension liner as a locking liner including features of the present invention.

FIG. 2 is a cross-sectional view taken along line II-II of FIG. 1.

FIG. 3 is a cross-sectional view taken along line III-III of FIG. 1.

FIG. 4 is a perspective view showing the liner according to FIG. 1 as a cushion liner.

Figure 5:
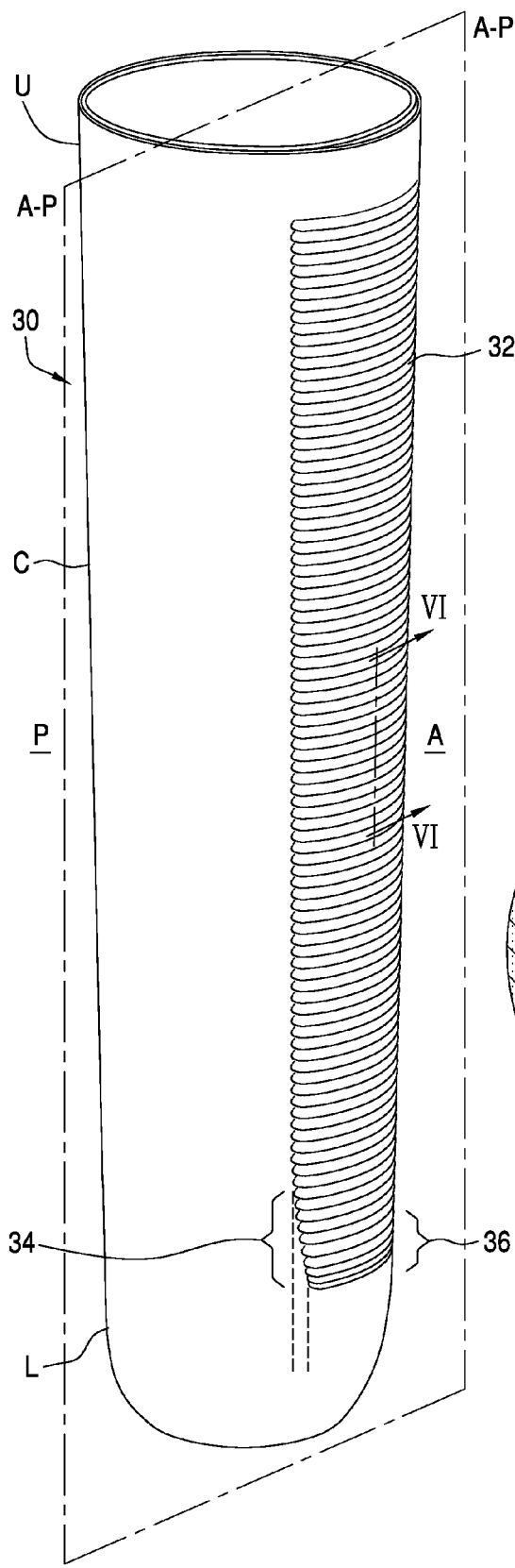
FIG. 5 is an elevational view of another embodiment of a suspension liner as a cushion liner.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary configurations of a liner, and in no way limit the structures or configurations of a liner thereof according to the present disclosure.

DETAILED DESCRIPTION OF VARIOUS EMBODIMENTS

A better understanding of different embodiments of the invention may be had from the following description read in conjunction with the accompanying drawings in which like reference characters refer to like elements.

FIGS. 1-4 illustrate an embodiment of a prosthetic suspension liner 10 having a multiple component system. The liner 10 defines a close-ended tubular sleeve having a longitudinal axis $X_L$-$X_L$, and is configured to envelop a distal area of a residual limb (not shown). The liner 10 defines an upper or proximal portion U, a lower or distal portion L, and a center portion C axially extending between the upper and lower portions U, L. The liner is also divided along an anterior-posterior A-P plane between anterior and posterior sides or aspects A, P of the liner.

An elasticized fabric or textile layer 12 continuously covers the outer surface 24 of the liner 10 without interruption. The liner is intended to be air-tight when donned over a residual limb. As illustrated in FIGS. 1 and 2, the liner may include a prosthesis connecting element 20, as would be understood by the skilled person in the field of prosthetic devices, when the liner is modified as a locking liner. FIGS. 4 and 5 depict the liner as a cushion liner without a connecting element.

The liner 10 includes a first component or layer 14 defined by a first elastomeric material. The first layer defines first and second opposed surfaces, such that the first layer 14 has a first surface which forms a circumferential internal surface 22 to the liner. The inner surface may be substantially smooth and continuous without interruption so as to facilitate donning of the liner on a residual limb. The liner 10 also includes a second component or layer 16 defined by a second elastomeric material. The first and second layers 14, 16 are contiguous and integrally joined to each other along only a portion of the second surface of the first layer 14. The interface between the layers 14, 16 is seamless and integrally permanent.

In observing the embodiments of FIGS. 3 and 4, the second layer 16 does not circumferentially extend about the liner 10, but instead the thickness is radially variable across the anterior aspect of the liner. In short, the second layer 16 is only provided in a localized region of the liner. According to this embodiment, the second layer 16 particularly corresponds to the tibial portion of the liner and extends along the anterior aspect A of the liner thereby providing additional comfort to the wearer along this region.

In this embodiment, the first layer 14 is stiffer than the second layer 16, and the first elastomeric material has a greater hardness than the second material. In other variations, the first and second layers may define different relationships regarding their respective hardness.

The combination of the first and second layers 14, 16 define different thicknesses at various regions of the liner, and these layers themselves may have different thicknesses over the liner.

In reference to FIGS. 2 and 3, the liner 10 defines a greater thickness at the tibial portion of the liner as represented by a side of the liner including the second layer 16 in combination with the first layer 14. Particularly, the anterior aspect A of the liner defines a thickness $t_1$ including both the first and second layers 14, 16 in combination with the fabric layer 12. The thickness $t_2$ at the posterior aspect P at or about the same height as the thickness $t_1$ is smaller than the thickness $t_1$.

The thickness $t_2$ includes only the first layer 14 in combination with the fabric layer 12, with the first layer 14 having a generally consistent circumferential thickness $t_6$ over at least the central portion C across both the anterior and posterior aspects A, P of the liner. It will be understood that the first layer 14 preferably has thickness $t_6$ extending over the second layer 16 in the lower portion L liner.

The lower portion L of the liner includes a cushioned region 18 having both the first and second layers 14, 16 wherein the second layer 16 has a greater thickness than at other portions, as evidenced by thicknesses $t_3$. As the second layer 16 terminates at the lower portion on the posterior aspect P of the liner, the thickness of the second layer gradually tapers so that the second layer 16 no longer exists and only the first layer 14 continues along the posterior aspect P of the liner. In particular, the thickness of the second layer 16 tapers as it extends from the anterior aspect A to the posterior aspect P across the lower portion L of the liner.

In particular reference to FIG. 3, the thickness $t_4$ of the second layer 16 on the anterior aspect A of the liner in the central and upper portions C, U is a radially variable, in that the thickness tapers toward the first or lateral, and second or medial sides of the liner. The second layer 16 may be formed along the entirety of the anterior aspect of the liner, or, as shown in FIG. 4, only along a strip of the anterior aspect of the liner and less than the entirety of the anterior aspect of the liner.

In order to illustrate the thickness differences in an exemplary embodiment of the suspension liner, the thickness $t_1$ formed by the combination of the textile layer and the first and second layers on the anterior aspect A of the liner may be 5.5-7.5 mm, the thickness $t_2$ may be 1.5-3.5 mm for the combination of the first layer and the textile layer, and the thickness at $t_3$ formed by the combination of the textile layer and first and second layers at the lower portion may be 10.0-14.0 mm and increase to a maximum at the longitudinal axis, tapering differently in thickness on both sides thereof.

The liner embodiment may be configured so that the second layer is particularly positioned at locations of the liner either including or excluding the anterior aspect A. According to one variation, the second layer defines a front outer portion of the liner and the first layer defines at least the rear outer portion of the liner. In this variation, the second layer extends over less than 50% of the total surface area of the second surface of the first layer. Of course, other ratios are available as long as the second layer extends less than the total surface area of the first surface of the first layer.

It should be noted that the liner is not limited to having the second layer only defined along the anterior aspect of the liner, and it is envisioned that the second layer may extend in part into the upper and center portions of the posterior aspect of the liner.

It will be noted that the liner may have a circumferential taper as the liner approaches a posterior end of the liner, as denoted by thickness $t_5$.

According to a variation in FIG. 4, the second layer circumferentially extends about a lower, closed-ended portion of the liner and, a spline 28 divides the first and second layers to provide a clear demarcation between the first and second layers preferably along the anterior aspect of the liner.

Turning to another embodiment of the liner, the second layer forms an undulating wall thickness along an elongated portion thereof. In a variation, the undulating wall thickness is formed only along the second layer, such that the first layer second surface and the second layer first surface are continuously devoid of the peripheral profiles. In another variation, the undulating wall thickness may be formed by both the first and second layers.

The undulating wall thickness may be formed only in the second layer. For example, in a liner designated for a trans-tibial amputee, the undulating wall thickness corresponds to the anterior aspect of the residual limb so as to facilitate the bending of the liner.

Figure 6:
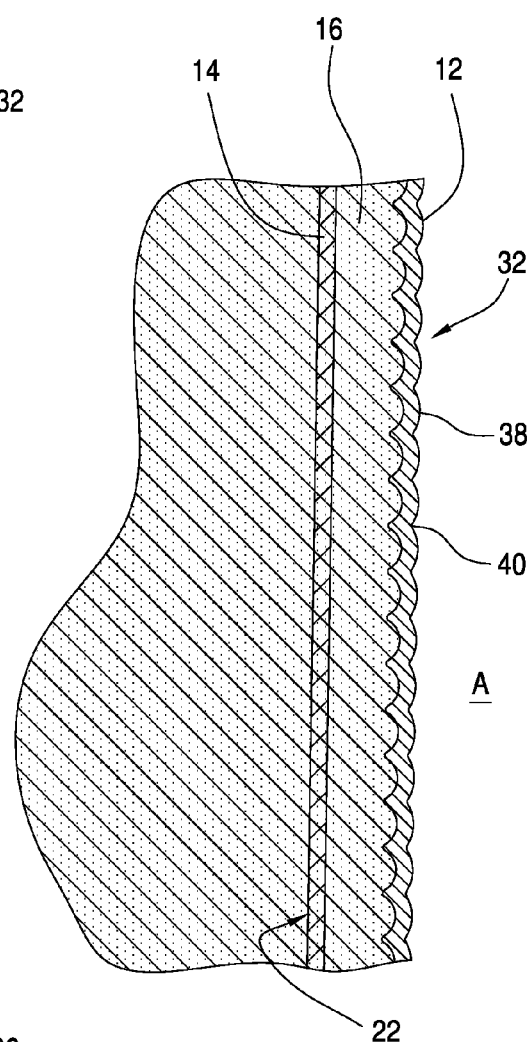
FIG. 6 is cross-sectional view of a cross-section view taken along line VI-VI of FIG. 5.

According to the embodiment depicted by FIGS. 5 and 6, a liner 30 defines a plurality of peripheral profiles 32 extending generally between the proximal and distal ends of the liner 30 generally along the anterior aspect A of the liner. According to this embodiment, the peripheral profiles are located only in the anterior aspect of the liner such that the proximal and distal ends and at least the posterior aspect P of the liner are devoid of the peripheral profiles.

As shown in FIGS. 5 and 6, the peripheral profiles 32 are defined as a plurality of adjacent projections that extend annularly about the axis of the liner 30. The projections 38 have a generally uniform, rounded outline, and are axially spaced at troughs 40 from one another. The projections 32 generally distend radially outwardly from the liner 30, and the internal surface 22 of the liner 30 is substantially smooth.

According to this embodiment, the peripheral profiles 32 are formed only in the second layer 16, whereas the first layer 14 lacks the peripheral profiles. The elasticized fabric 12 generally follows the contours of the peripheral profiles 32.

FIG. 5 shows a variation of a liner having the peripheral profiles in that a plurality of profiles 34 taper in width as they draw closer to the distal end of the liner. In addition, FIG. 5 shows a plurality of profiles 36 having a taper in height as they draw closer to the distal end of the liner. In other variations, the peripheral profiles may have varying thicknesses and different spacing along the liner. The liners according to the invention may either omit or have any combination of these peripheral profiles described herein and described in U.S. Pat. No. 7,118,602, incorporated herein by reference.

While in each of the liner embodiments described above the distal portion is generally without peripheral profiles, liner embodiments of the invention may be configured so that at least a section of the distal portion may be provided with peripheral profiles such as those discussed above. It will be noted that embodiments of the liner may have variable wall thicknesses at least in regions of the peripheral profiles. Such variable wall thickness improves the ability to stretch the liner and additionally provides cushioning by more aptly distributing pressure against a prosthesis such as a hard socket.

Moreover, the peripheral profile portions of the liners may be combined or modified as considered expedient by one of ordinary skill in the art to improve stretchability and comfort for an amputee.

In each of the embodiments shown herein, the liner is intended for use between a residual limb and a prosthesis, such as a hard socket, and to be air-tight when donned over a residual stump. The internal surface of the liner may be formed of a layer of silicone elastomer, therefore serving as a skin interface. Silicone is advantageous in that it allows for different levels of softness and strength to be incorporated into the liners of the present application. Moreover, silicone permits the addition of selected supplements, such as petroleum jelly and aloe vera, which improve skin care and comfort.

An elasticity controlling matrix material may be provided on the exterior of the liner, the matrix material preferably being relatively compliant in a radial direction and substantially rigid or inelastic in an axial direction. The matrix material may extend over the distal or external side of the prosthesis, and is advantageous in that it prevents movement of the liner when a prosthesis is worn thereover.

It is envisioned that any of the aforementioned liners, and subsequently discussed sleeves, may be constructed having a soft internal silicone elastomer layer and a relatively harder external silicone elastomer layer in accordance with U.S. Pat. No. 6,136,039, incorporated herein by reference.

A prosthesis connecting element, as shown in FIG. 2, may be provided at the distal end of any of the embodiments of the inventive liner of the present application. The connecting element may be embedded in a silicone elastomer layer or layers of the liner, or may be intimately bonded to the distal end of the liner. An example of a connecting element is discussed in U.S. Pat. No. 6,136,039. Alternatively, the liner may be provided without a connecting element, and have a distal end portion with enhanced cushioning as in what is commonly known as a "Cushion" type liner.

A liner in accordance with this disclosure may be fabricated in a sufficient number of sizes to accommodate various sizes of residual limbs. In use, a liner of the type described herein is rolled up from the proximal to the distal end, placed over the distal end of the residual stump and rolled back up or "donned" over the stump like a stocking. This procedure and the benefits achieved thereby are described in detail in U.S. Pat. No. 4,923,474, incorporated herein by reference. In addition, any of the liners and sleeves mentioned herein may be constructed in the manner prescribed by U.S. Pat. No. 4,923,474.

Any of the liner embodiments described herein may include a sealing arrangement, as taught in any one of U.S. Pat. Nos. 7,025,793 and 7,749,281, and U.S. patent application publication 2007/0123998, each of which is incorporated herein by reference.

The embodiments of the inventive liner of the present application may be constructed according to the molding methods described in U.S. Pat. No. 6,485,776, the entirety of which is incorporated herein by reference. In making the liners having peripheral profiles, the profiles may be imparted to the liner by appropriate molding techniques, such as female molds which have the impression of the desired peripheral profiles of the invention.

Of course, it should be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct suspension liner in accordance with principles of the present invention.

Although this invention has been disclosed in the context of certain exemplary embodiments and variations thereof, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. A suspension liner for a residual limb, the liner forming a closed-ended, tubular sleeve having a longitudinal axis, and defining along the axis a lower portion, an upper portion, and a center portion extending between the lower and upper portions, the liner divided along an anterior-posterior plane between anterior and posterior aspects, the liner comprising:
a first layer having first and second surfaces spaced by a first thickness, the first surface forming a continuous circumferential internal surface of the liner and configured for contacting skin of a residual limb;
a second layer having a first surface being adjacent and integrally joined to the first layer second surface, the second layer extending across the upper, central and lower portions of the anterior aspect of the liner, and terminating at the lower portion of the posterior aspect of the liner, a variable radial thickness tapers toward lateral and medial sides of the liner from the anterior aspect over a cross-sectional slice of the liner inwardly toward the longitudinal axis relative to an outer peripheral surface of the liner;
wherein the second layer axially tapers in thickness along the posterior side above the lower portion of the liner toward the upper portion of the liner such that a length of the first layer extending beyond said tapered second layer thickness is devoid of the second layer thereagainst in the direction of the upper portion;
wherein at the cross-sectional slice of the liner the radial taper of the second layer reduces to nothing toward the posterior side of the liner at the same point whereat the first layer is devoid of the second layer.

2. The suspension liner of claim 1, wherein the second layer extends across the entirety of the lower portion of the liner.

3. The suspension liner of claim 1, wherein the first layer is stiffer than the second layer.

4. The suspension liner of claim 1, wherein the second layer forms an undulating wall thickness only along an elongated portion thereof across the upper and central portions of the anterior aspect of the liner.

5. The suspension liner of claim 1, further comprising a fabric or textile layer continuously covering the outer peripheral surface of the liner.

6. The suspension liner of claim 1, further comprising a connecting element located at lowermost end of the liner.

7. The suspension liner of claim 1, wherein an internal surface of the liner is substantially smooth.

8. The suspension liner of claim 1, wherein the outer peripheral surface of the liner at the lower portion defines a continuously sloping profile devoid of projections and extends to a lowermost portion of the liner.

9. A suspension liner for a residual limb, the liner forming a closed-ended, tubular sleeve having a longitudinal axis, and defining along the axis a lower portion, an upper portion, and a center portion extending between the lower and upper portions, the liner divided along an anterior-posterior plane between anterior and posterior aspects, the liner comprising:
a fabric or textile layer continuously covering an outer peripheral surface of the liner;
a first layer defined by a first elastomeric material and having first and second surfaces spaced by a first thickness, the first surface forming a continuous circumferential internal surface of the liner and configured for contacting skin of a residual limb;
a second layer defined by a second elastomeric material, the second layer first surface being adjacent and integrally joined to the first layer second surface, the second layer extending across the upper, central and lower portions of an anterior aspect of the liner, and terminating at the lower portion of a posterior aspect of the liner;
wherein the first layer has a continuously uniform circumferential thickness and the second layer has a variable radial thickness along a cross-sectional slice of the liner over the anterior aspect of the liner and tapers toward lateral and medial sides of the liner from the anterior aspect, a posterior side thickness of the second layer at a predetermined height of the liner being less than an anterior side thickness of the second layer at the same predetermined height, said variable radial thickness of the second layer projects relatively inwardly from the outer peripheral surface of the liner toward the longitudinal axis of the liner;
wherein the first elastomeric material has a greater stiffness than the second elastomeric material;

wherein the second layer thickness axially increases to a maximum at the lower portion and said maximum thickness is generally aligned along the longitudinal axis of the liner.

10. The suspension liner of claim 9, wherein the outer peripheral surface of the liner at the lower portion defines a continuously sloping profile devoid of projections and extends to a lowermost portion of the liner.

11. The suspension liner of claim 9, further comprising a connecting element located at lowermost end of the liner.

12. The suspension liner of claim 9, wherein an internal surface of the liner is substantially smooth.

\* \* \* \* \*